(12) United States Patent
Taki et al.

(10) Patent No.: US 7,928,236 B2
(45) Date of Patent: Apr. 19, 2011

(54) FLUORESCENT AMINO ACID DERIVATIVES

(75) Inventors: Masumi Taki, Okayama (JP); Masahiko Sisido, Okayama (JP)

(73) Assignee: National University Corporation Okayama University, Okayama (JP)

( * ) Notice: Subject to any disclaimer, the term of this patent is extended or adjusted under 35 U.S.C. 154(b) by 688 days.

(21) Appl. No.: 11/916,061

(22) PCT Filed: Jun. 8, 2006

(86) PCT No.: PCT/JP2006/311561
§ 371 (c)(1),
(2), (4) Date: Jan. 14, 2008

(87) PCT Pub. No.: WO2006/132335
PCT Pub. Date: Dec. 14, 2006

(65) Prior Publication Data
US 2010/0152417 A1 Jun. 17, 2010

(30) Foreign Application Priority Data

Jun. 10, 2005 (JP) ................................ 2005-171019

(51) Int. Cl.
*C07D 221/18* (2006.01)
*A61K 38/02* (2006.01)
(52) U.S. Cl. ............ 546/61; 530/350; 530/331; 514/2.1
(58) Field of Classification Search .................... 546/61; 530/331, 350; 514/2, 2.1
See application file for complete search history.

(56) References Cited

FOREIGN PATENT DOCUMENTS
WO    WO 02/099424 A2    12/2002

OTHER PUBLICATIONS

Szymanska et al., "Synthesis of N-[(tert-Butoxy)carbonyl]-3-(9,10-dihydro-9-oxoacridin-2-yl)-L-alanine, a New Fluorescent Amino Acid Derivative," Helvetica Chimica ACTA, vol. 86 (2003) pp. 3326-3331.
International Preliminary Report on Patentability (in English) for PCT/JP2006/311561 dated Dec. 27, 2007.

*Primary Examiner* — Charanjit S Aulakh
(74) *Attorney, Agent, or Firm* — Kilyk & Bowersox, P.L.L.C.

(57) ABSTRACT

The subject of the present invention is to provide a fluorescent substance excitable under visible light, having higher photostability and a long fluorescence lifetime. Another subject is to provide a fluorescent substance consists of a non-natural amino acid applicable to peptide synthesis systems.

Searching fluorescent substances, which are fluorescent amino acids and excitable under visible light, having the lowest possible molecular weight for a high photostability resulted in forming a condensed polycyclic aromatic compound by subjecting a compound having an acridone structure to substitution with an amino acid and further condensation with a benzene ring. Thus, the subject is achieved by the fluorescent substance consisting of amino acid-substituted benzoacridone derivative excitable under visible light.

11 Claims, 3 Drawing Sheets

FLUORESCENT AMINO ACID DERIVATIVES

This application is a National Stage Application of PCT/JP2006/311561, filed Jun. 8, 2006, which claims priority to JP 2005-171019 filed Jun. 10, 2005.

TECHNICAL FIELD

The present invention relates to novel fluorescent amino acid derivatives useful as a fluorescent marker. Specifically, it relates to amino acid-substituted benzoacridone derivatives excitable under visible light.

This application claims priority of Japanese Patent Application No. 2005-171019, the contents of which are hereby incorporated by reference.

BACKGROUND ART

In the case of investigating kinetics of biomolecules such as proteins, or in investigating interactions between biomolecules, a method for measurement of fluorescence intensity is often employed by labeling the analytes through with the use of phosphorescent or fluorescent dyes. Those fluorescent dyes such as Alexa Fluor, BODIPY FL, Cascade Blue, FITC, Oregon Green, RITC, Texas Red, TRITC, Coumarin Maleimide, Cy Dye, Dansyl Chloride and Dansyl Hydrazine can be used.

By synthesizing non-natural amino acids having functional side chain, by introducing them into proteins at specific positions as the same manner as natural amino acids or by introducing into peptides using peptides synthesizing system, various kinds of functional groups can be introduced into proteins without suppressing their functions. For example, the analyses of kinetics of biomolecules and interactions between them are expected to be carried out simply and accurately, if the incorporation of a non-natural amino acid(s) at specific positions of proteins or the application of a non-natural fluorescent amino acid(s) to the peptides using peptides synthesizing system is performed.

To conduct measurements using conventional instruments, such as a confocal microscope and a microplate reader, subject fluorescent dyes must show absorption wavelengths in visible light range. As widely known fluorescent dyes excitable under visible light may have an extremely large molecular structure, they are inappropriate for fluorescence labeling using protein synthesizing system. Further, when labeling proteins, some of the conventional fluorescent substances have problems in terms of photo stability, easy to inactivate, and high tendency for quenching, during monitoring the kinetics and interactions of the labeled biomolecules.

There is a report on the synthesis of a fluorescent amino acid having an acridine structure (Non-patent document No. 1). Derivatives of a novel acridone dye having a characteristic fluorescence lifetime have been disclosed (Patent document No. 1). Further, patent document No. 1 reported on other acridone dye derivatives, wherein a set of different fluorescent acridone dye derivatives, each of which has a different fluorescence lifetime, is especially useful in multiparameter analysis. However, fluorescent amino acids or acridone dyes derivatives reported in them are fluorescent substances appropriate for use under primarily UV light for excitation. Meanwhile, BODIPY® (Invitrogen), which is a fluorescent substance excitable under visible light and having higher photostability, is commercially available. The compound has a high molar extinction coefficient and high molecular fluorescence yield, thereby being able to emit strong fluorescence, but it is difficult to introduce it into proteins, because it has large-size side chain and it may break the higher-order structure of the proteins.

[Non-patent document No. 1] Helvetica Chimica Acta., 86, 3326 (2003)

[Patent document No. 1] JP 2005-500406 A

DISCLOSURE OF THE INVENTION

Problem to be Solved by the Invention

The subject of the present invention is to provide fluorescent substances excitable under visible light, having high photostability and long fluorescence lifetime. Another subject is to provide fluorescent substances consisting non-natural amino acids applicable to peptides synthesis systems.

Means for Solving the Problem

Strenuous study and search by the inventor of the present invention for fluorescent substances, which are fluorescent amino acids, excitable under visible light and having the lowest possible molecular weight for higher photostability resulted in forming condensed polycyclic aromatic compounds by subjecting compounds having acridone structures to substitution with amino acids and further condensation with benzene rings. Thus, the inventors of the present invention successfully achieved fluorescent substances capable of solving the above problem and completed the invention.

Thus, the present invention comprises the followings:

1. A fluorescent substance consisting of amino acid-substituted benzoacridone derivative excitable under visible light.
2. The fluorescent substance according to the preceding aspect 1, wherein the maximum absorption wavelength of a mixture of water and ethanol (at a volume ratio of 1:1) is in the range of 420 to 520 nm.
3. The fluorescent substance according to either preceding aspect 1 or 2, wherein the amino acid-substituted benzoacridone derivative is alanine-substituted benzoacridone derivative.
4. The fluorescent substance according to the preceding aspect 3, wherein the alanine-substituted benzoacridone derivative is represented by one of the following formulae from (I) to (III):

[Chem. 1]

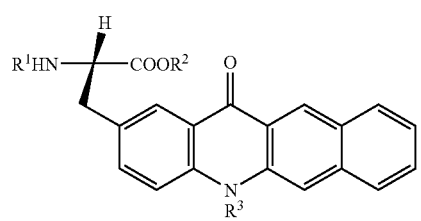

Formula I

[Chem. 2]

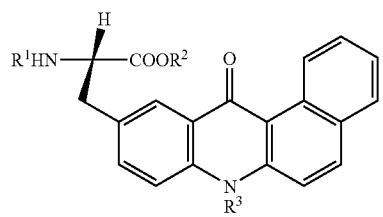

Formula II

[Chem. 3]

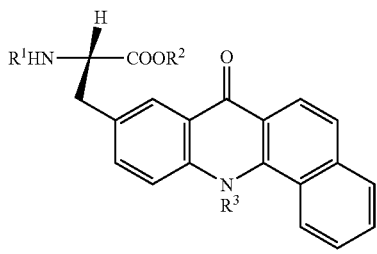

Formula III wherein the formulae from (I) to (III):

$R^1$ represents a hydrogen atom or an amino protecting group, $R^2$ represents a hydrogen atom or carboxylate ester structure and $R^3$ represents a hydrogen atom, or a straight or branched, saturated or unsaturated aliphatic hydrocarbon group; cycloalkyl, aryl, aralkyl, alkyloxy, alkenyloxy, alkynyloxy, aryloxy or aralkyloxy group which may have substituent(s); or sugar residue.

5. A reagent comprising the fluorescent substance according to any one of the preceding aspects 1 to 4.
6. A fluorescent peptide chain or protein, wherein the fluorescent substance according to any one of the preceding aspects 1 to 4 is incorporated at either its C- or N-terminal or in its interior.
7. The peptide chain or protein according to the preceding aspect 6, further comprising other fluorescent or quenching substance capable of interfering with the fluorescent substance according to any one of the preceding aspects 1 to 4.
8. A production method of the fluorescent substance according to any one of the preceding aspects 1 to 4, comprising a step using $Cu_2O$ and ethyleneglycol monoalkyl ether in coupling of a halonaphthalene derivative and 3-(4-aminophenyl)-2-tert-butoxycarbonylamino-propionate ester.
9. The production method according to the preceding aspect 8, wherein the halonaphthalene derivative is 3-chloronaphthalene-2-carboxylic acid, the 3-(4-amino-phenyl)-2-tert-butoxycarbonylamino-propionate ester is 3-(4-aminophenyl)-2-tert-butoxycarbonylamino-propionic acid ethyl ester, and the ethyleneglycol monoalkyl ether is methoxyethanol.

Effects of the Invention

The amino acid-substituted benzoacridone derivatives of the invention are fluorescent substances excitable under visible light and have higher photostability. The amino acid-substituted benzoacridone derivatives of the invention are hereinafter sometimes referred to as simply "the fluorescent substances of the invention". The fluorescent substances of the invention can be used as Boc- or Fmoc-protected fluorescent amino acids, and fluorescent peptides in large amounts can be synthesized with them through an automatic peptide synthesizer. Fluorescent peptides are broadly used in, for example, various analyses and examinations. For example, the fluorescent substances of the invention and an existing fluorescent substances which have absorption and emission wavelengths in the different wavelength range of the fluorescent substances of the invention can be incorporated into one molecule of peptide or protein for inducing fluorescence resonance energy transfer (FRET). Further, an existing electron acceptor and the fluorescent substance of the invention can be incorporated into one molecule of peptide or protein for inducing intramolecular electron transfer quenching. Such electron transfer quenching is useful in sensing, analyses of protease actions and the like. In that case, the emission of fluorescence is restored by the cleavage of the peptide or protein. Further, as the fluorescent substances of the invention have long fluorescence lifetime, the fluorescence emission of the fluorescent substances of the invention would be maintained for a long time, even after the background fluorescent noise of the biological sample is decreased when a target substance is detected in not well-purified biological samples. Therefore, the fluorescent substances of the invention are useful for detection with high sensitivity through time-resolved measurement.

DESCRIPTION OF THE PREFERRED EMBODIMENT

Figure 1:
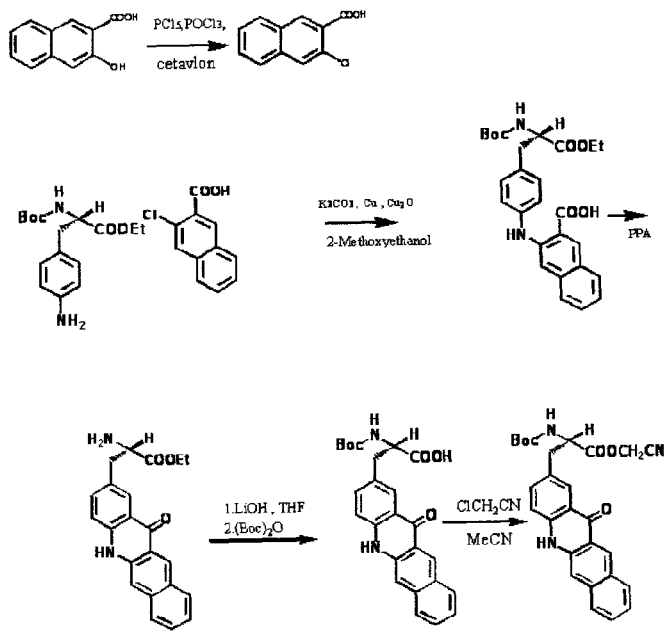
FIG. 1 shows the synthesis schemes of alanine-substituted benzoacridone derivatives.

Amino acids employed for the substitution of the amino acid-substituted benzoacridone derivatives of the invention are preferably, but are not limited in particular to, neutral amino acids, and more preferably amino acids having relatively lower molecular weight. Among such amino acids, the most preferred is alanine. Further, the amino acid for the substitution may be an amino acid itself, but inconsideration of stability, ease of handling and the like, amino acid derivatives having protecting group or various substituents may be employed.

In particular, alanine-substituted benzoacridone derivatives represented by any one of the following formulae from (I) to (III) may be mentioned. In the formulae from (I) to (III), $R^1$ represents a hydrogen atom or an amino protecting group, and $R^2$ represents a hydrogen atom or carboxylate ester structure. Examples of amino protecting groups include, but are not limited in particular to, acetyl, benzoyl, benzyloxycarbonyl, tosyl or t-butoxycarbonyl group (Boc), and 9-fluorenylmethoxycarbonyl (Fmoc) group. The examples of structures of carboxylate ester include, but are not limited in particular to, substituted or unsubstituted alkyl esters (for example, methyl and ethyl esters) and arylalkyl esters (for example, benzyl and p-methoxybenzyl esters), which may comprise nitro, cyano and other groups. $R^3$ represents a hydrogen atom, or a straight or branched, saturated or unsaturated aliphatic hydrocarbon group; cycloalkyl, aryl, aralkyl, alkyloxy, alkenyloxy, alkynyloxy, aryloxy or aralkyloxy group which may have substituent(s); or sugar residue. Herein, the reaction residue of sugar means a sugar having a structure wherein one hydroxy group is detached from a sugar molecule by the reaction between sugar and a benzoacridone derivative. The sugars include monosaccharides, disaccharides and polysaccharides, and in particular, monosaccharides such as glucose, fructose and galactose, and disaccharides such as maltose, sucrose, lactose and trehalose are preferred. The compounds represented by formulae from (I) to (III) include L-type, D-type or racemic compounds, and L-type is preferred.

[Chem. 4]

Formula I

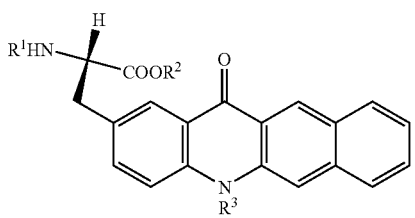

[Chem. 5]

Formula II

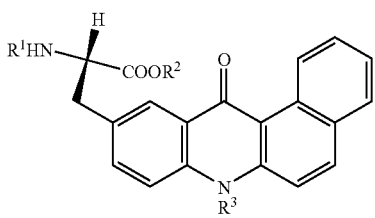

[Chem. 6]

Formula III

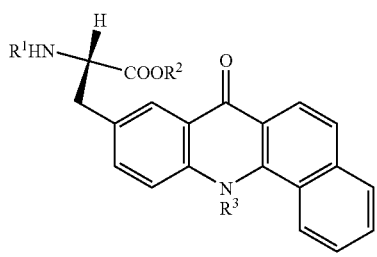

The fluorescent substances of the invention are excited by visible light, for example, a mixture of water and ethanol (at a volume ratio of 1:1) has the maximum absorption wavelength range of 420 to 520 nm, preferably they are excited in the range of 450 to 490 nm, and in particular, by wavelengths of 455 nm, 468 nm, 488 nm and the like. Further, according to the fluorescence spectra of the fluorescent substances of the invention, they emit fluorescence at wavelengths of 500 to 600 nm, especially 500 to 525 nm.

The fluorescent substances of the invention can be used for labeling various target biological materials to confer fluorescence properties. As the fluorescent substances of the invention are amino acid-substituted, they can be used as Boc- or Fmoc-protected fluorescent amino acids for synthesizing fluorescent peptides in large amounts through an automatic peptide synthesizer. Peptides can be synthesized by a well known method per se. Further, the fluorescent substances of the invention can be incorporated into proteins by a well known method per se.

Fluorescent peptides can be used as, for example, fluorescent peptide probes, synthetic substrates, quenchable fluorescence substrates and the like. For example, in the case of fluorescent peptide probes, they can be used as sensor molecules to detect changes in the property of fluorescence resonance energy transfer (FRET), which are regarded as the structural changes of the peptide. Further, an existing electron acceptor and the fluorescent substance of the invention can be incorporated into one molecule of peptide or protein for inducing intramolecular electron transfer quenching. Such electron transfer quenching is useful in sensing, analyses of protease actions and the like. In that case, the emission of fluorescence is restored by the cleavage of the peptide or protein. Further, the fluorescent peptide probes can be subjected to antigen-antibodies reaction as an antigen to analyze interactions between antibody and antigen, and also interactions between a receptor of a particular protein and the protein of interest in the same manner.

Fluorescent substrate for FRET can be prepared by incorporating the fluorescent substance of the invention into a peptide chain at specific position either its C- or N-terminal or in its interior and synthesizing a fluorescent peptide chain containing other fluorescent substance capable of interfering with the fluorescent substance described above. The examples of other fluorescent substances capable of interfering with the fluorescent substances of the invention, include the fluorescent substances having the maximum absorption wavelength in the wavelength range shorter than 420 nm and the emission wavelength range from 420 to 500 nm, and in particular, the fluorescent substance having a scaffold of anthracene, 10H-acridin-9-one or 2-(Methyl)amino-benzamide (Taki et al., Nuc. Acid. Res. Supl., 203-204 (2002)), or 2-aminobenzamide (Taki et al., FEBS Lett., 35-38, 507 (2001)) may be mentioned. Further, the other examples of other fluorescent substances capable of interfering with the fluorescent substances of the invention may also include those having the maximum absorption wavelength in the wavelength range longer than that of the fluorescent substances of the invention. Proteases' action can be analyzed by employing interference effects with the fluorescent substance of the invention and other fluorescent substance capable of interfering with the invented substance, by synthesizing a peptide, which has an amino acid sequence, such as to be cleaved by particular proteases at specific points between the fluorescent substances.

While fluorescent peptides having currently existing fluorescent substances have already put to practical use, more useful fluorescent peptides can be synthesized by the fluorescent substances of the invention.

As the fluorescent substances of the invention are excited by the visible light range as described above, they can be measured and detected in various ways using general-purpose analyzers. Meantime, biological samples contain many impurities, suggesting that the impurities except for analyte may contain fluorescent substances. Therefore, decreasing the background noise in measuring systems has been an important subject. Lifetimes of fluorescences emitted by impurities in biological samples are for around 0 to 5 nanoseconds, while that of the fluorescent substances of the invention are for around 10 to 20 nanoseconds. When the fluorescent substances of the invention are employed in analyses such as various measurements and detections, the fluorescence of a measuring subject labeled with the fluorescent substance of the invention can be detected after fluorescence of impurities are quenched. Thereby, detection systems having a specific property and high sensitivity can be established under the condition of decreased background noises.

In this way, the fluorescent substances of the invention can be incorporated into one molecule of peptide and protein. The fluorescent substances of the invention can be provided as fluorescent reagents for preparing such fluorescent peptides and proteins.

FIG. 1 shows representative schemes of method for synthesizing the fluorescent substance of the invention.

In FIG. 1, 3-chloro-naphthalene-2-carboxylic acid is a specific example of a halonaphthalene derivative. Further, 3-(4-amino-phenyl)-2-tert-butoxycarbonylamino-propionic acid ethyl ester is a specific example of 3-(4-amino-phenyl)-2-tert-butoxycarbonylamino-propionate ester.

In the production process of an amino acid-substituted benzoacridone derivatives, the present invention is characterized by using Cu₂O and ethyleneglycol monoalkyl ether in a coupling step between halonaphthalene derivatives and 3-(4-amino-phenyl)-2-tert-butoxycarbonylamino-propionate ester. Compared to conventional coupling methods using dimethylformamide (DMF) and Cu, the method using Cu₂O and ethyleneglycol monoalkyl ether can greatly improve its yield. In that case, as a specific example of ethyleneglycol monoalkyl ether, methoxyethanol may be mentioned.

EXAMPLES

The fluorescent substances of the invention will be explained in the examples below using an alanine-substituted benzoacridone derivatives as an example, and, in particular, the synthesis method, properties and the like of the present fluorescent substance will be explained, but will not be limited to them and various modifications may be applied to them without departing from the technical concept of the present invention.

Example 1

Synthesis of Alanine-Substituted Benzoacridone Derivatives

1) Synthesis of 3-chloro-naphthalene-2-carboxylic acid

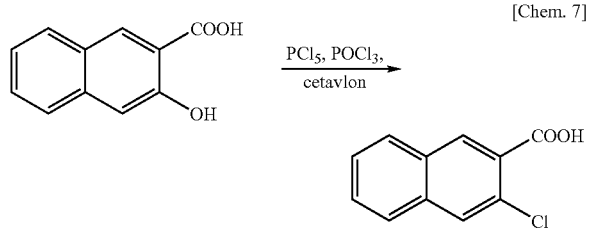

[Chem. 7]

$POCl_3$ was added to $PCl_5$, and then dried 3-hydroxy-naphthoic acid was added. Approximately a spatula of cetavlon was added, and after degassing by $N_2$ (nitrogen), the solution was heated to between 170 and 180° C. for 8 hours under reflux. After the reaction, the reaction solution was dropped portionwise on ice, observing yellow-white substance. Then, after heating to 60-70° C. for completing the reaction, centrifugation was performed at 3000 rpm for 5 minutes to collect the precipitate. A trace amount of ammonia solution and an appropriate amount of distilled water were added to the collected precipitate for dissolving the precipitate, and then the resulting solution was centrifuged at 3000 rpm for 3 minutes. The supernatant liquid obtained after centrifugation was added dropwise to a solution of 0.25 N hydrochloric acid. The pH of the solution was confirmed acidic then. The solution containing precipitates and suspended substance was centrifuged for another 5 minutes at 3000 rpm to collect the precipitate. The collected precipitate was recrystallized from ethanol and distilled water.

The recrystallized product was washed with distilled water, and then dried thoroughly. The product was analyzed by the EI-MASS spectroscopy, and obtains 3-chloro-naphthalene-2-carboxylic acid (CNCA).

2) Synthesis of Boc-3-(4-nitro-phenyl)-2-tert-butoxycarbonylamino-propionic acid ethyl ester (Boc-ntrPhe-OEt)

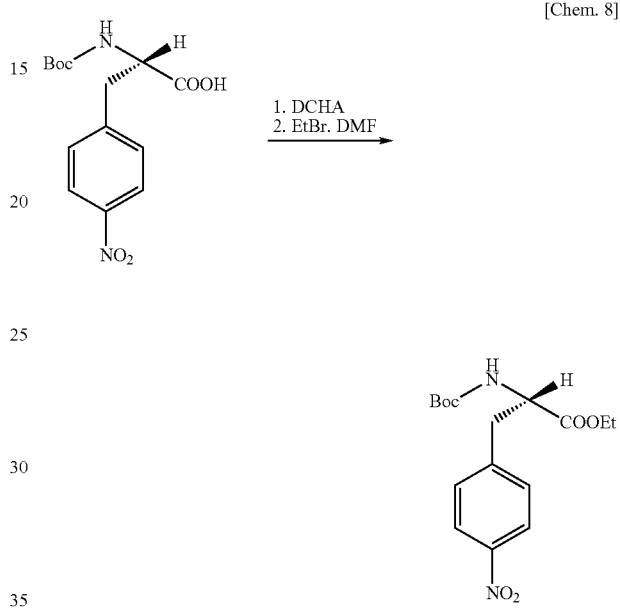

[Chem. 8]

Boc-ntrPhe was dissolved in a small amount of ethyl acetate, dicyclohexylamine (DCHA) was added portionwise, and then the solution was stirred at room temperature to deposit Boc-ntrPhe-OH.DCHA. 7.5 g of the obtained crystal (15.3 mmol), 8.5 ml of ethyl bromide (EtBr) (114 mmol) and 25 ml of dimethylformamide (DMF) were mixed and stirred overnight. The solvent was removed on an evaporator and the obtained substance was analyzed by ¹H-NMR spectroscopy. As a result, characteristic peaks of ethyl group appeared around 4.2 and 1.3 ppm, indicating the successful synthesis of Boc-ntrPhe-OEt.

3) Hydrogen conversion reaction of Boc-3-(4-nitro-phenyl)-2-tert-butoxycarbonylamino-propionic acid ethyl ester (Boc-ntrPhe-OEt)

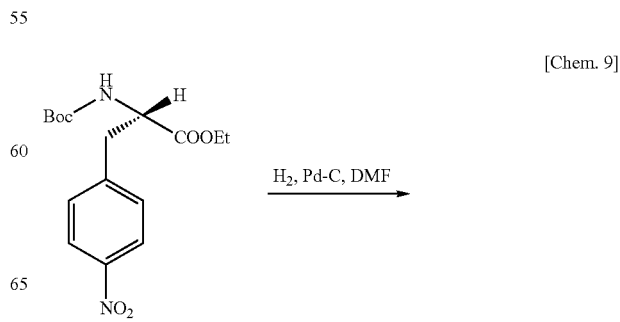

[Chem. 9]

-continued

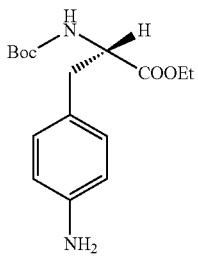

1 g of Boc-ntrPhe-OEt, 30 ml of DMF and 0.05 g of palladium-carbon (Pd—C) were mixed, gas-filling by hydrogen was conducted using a balloon, and the solution was stirred for approximately 8 hours. During the stirring, hydrogen was changed every 2 hours. The product was analyzed by $^1$H-NMR spectroscopy.

4) Ullmann coupling between Boc-aminoPhe-OEt and 3-chloro-naphthalene-2-carboxylic acid

[Chem. 10]

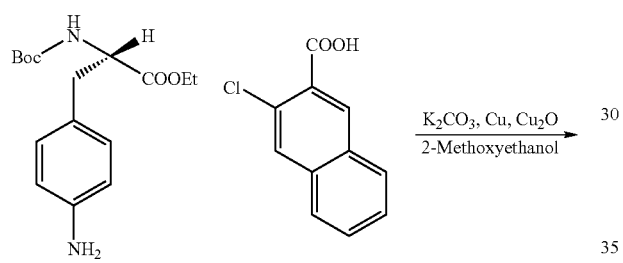

According to Table 1, reagents except for 2-methoxyethanol were mixed. Flask was subjected to degassing by nitrogen, added with 2-methoxyethanol, and heated to 120° C. under reflux. One and a half hours later, the reaction was terminated when the spot which corresponds to CNCA was disappeared on TLC developed by a mix solvent (ethyl acetate and hexane (2:1)). The reaction solution was filtered through cotton and sellite to remove Cu. The obtained filtrate was dropped into 15 ml of distilled water. The suspension that observed precipitate, was centrifuged at 3000 rpm for 5 minutes to collect the precipitate. This precipitate was dissolved in ethyl acetate, and washed two times with respectively 5% $KHSO_4$, 4% $NaHCO_3$ and saturated NaCl. After dehydration using $MgSO_4$, column purification was conducted. The column purification was conducted using developing solvents in the following order: chloroform and methanol (8:2)→chloroform and ethyl acetate (9:1)→chloroform and methanol (95:5). The obtained purified product was analyzed by $^1$H-NMR for identification. While comparative example 1 as shown below used DMF and Cu for coupling, obtaining extremely low yield, a substantial improvement was shown in the yield, with the yield of the target substance being 205.7 mg and 57% in the case where $Cu_2O$ was added and methoxyethanol was used for solvent, this time.

TABLE 1

|  | M. W | mg | mmol | mL | mol. ratio |
|---|---|---|---|---|---|
| Boc-aminoPhe-OEt | 338.36 | 80 | 0.24 |  | 2 |
| CNCA | 206.62 | 50 | 0.24 |  | 2 |
| $K_2CO_3$ | 138.21 | 17 | 0.12 |  | 1 |
| Cu | 63.55 | 5 |  |  |  |
| $Cu_2O$ | 143.09 | 5 |  |  |  |
| 2-Methoxyethanol |  |  |  | 0.5 |  |

5) Freidel Cyclization Reaction

[Chem. 11]

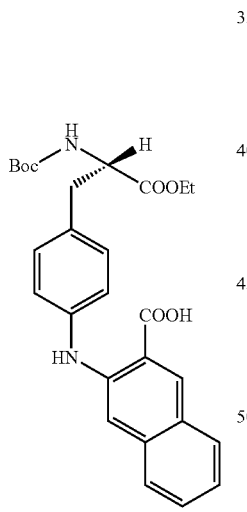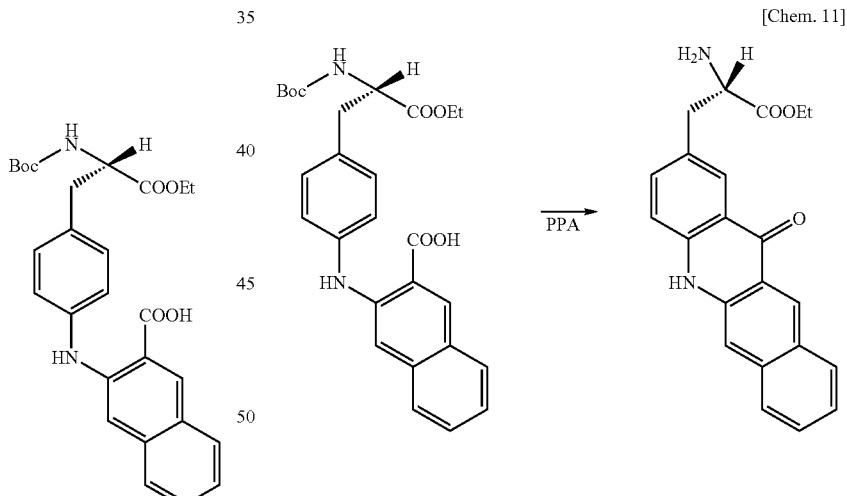

Figure 2:
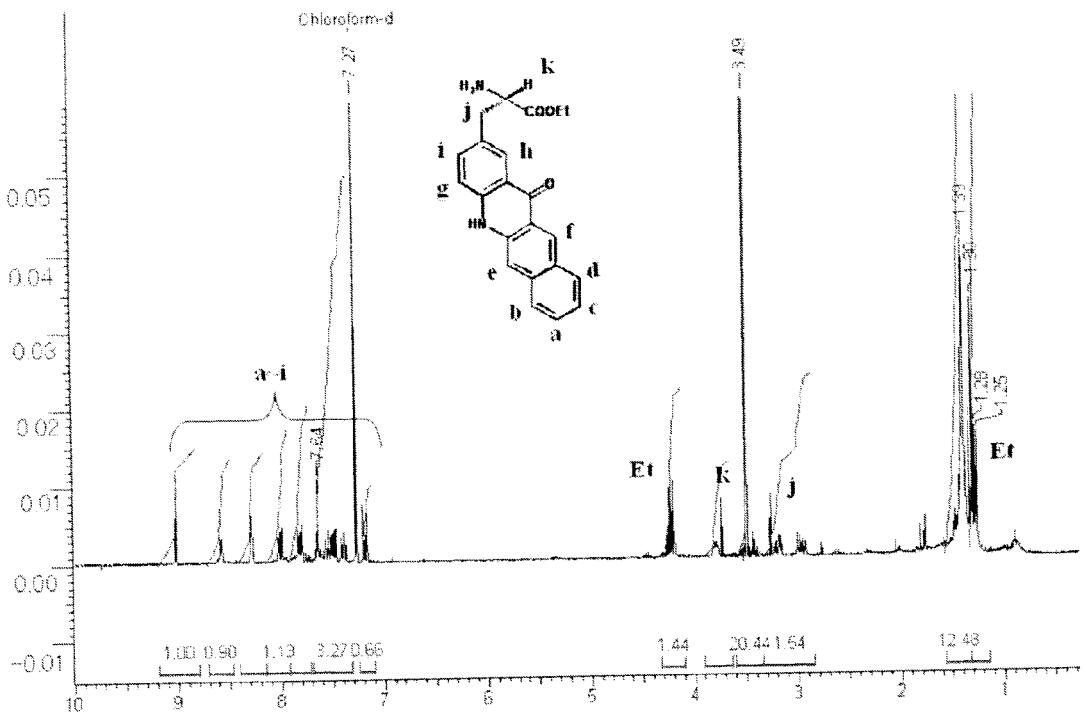
FIG. 2 shows the analytical result of $^1$H-NMR of an alanine-substituted benzoacridone derivative. (Example 1)

5.1 mg of polyphosphoric acid (PPA) (2.5 ml) heated to 60° C. in oil bath was added to 200 mg of Boc-aminoPhe-OEt.C-NCA and stirred to react for an hour at 80° C. Then, the reaction solution was added to distilled water, its pH was adjusted to 9 to 10 with 5% $NaHCO_3$, and then extraction was performed with ethyl acetate. The ethyl acetate extraction solution was examined with a developing solvent (dichloromethane and methanol (9:1)), showing roughly one spot at around Rf=0.6. After dehydration over $MgSO_4$, the solvent was removed on an evaporator. The product was analyzed by $^1$H-NMR and identified to be alanine-substituted benzoacridone derivative (badAla-OEt) (FIG. 2).

Comparative Example 1

Ullmann coupling between Boc-aminoPhe-OEt and 3-chloro-naphthalene-2-carboxylic acid

[Chem. 12]

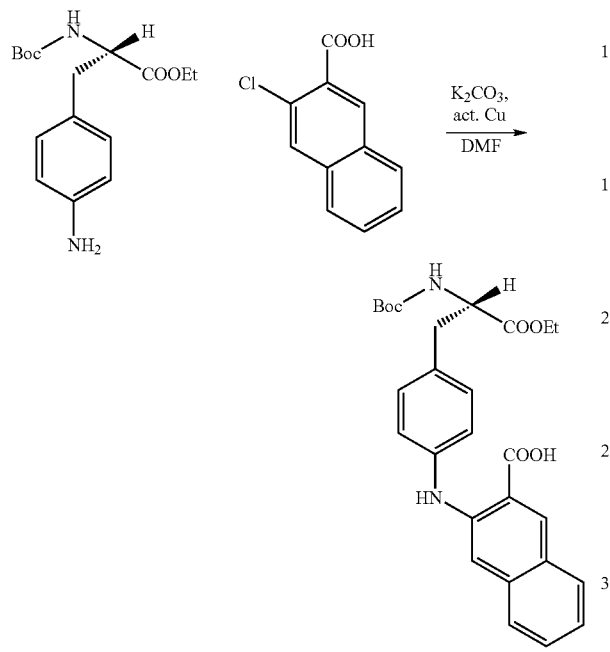

In the synthesis of alanine-substituted benzoacridone derivative, 1) synthesis of 3-chloro-naphthalene-2-carboxylic acid, 2) synthesis of 3-(4-nitro-phenyl)-2-tert-butoxycarbonylamino-propionic acid ethyl ester, and 3) hydrogen conversion reaction of 3-(4-nitro-phenyl)-2-tert-butoxycarbonylamino-propionic acid ethyl ester were conducted in the same manner as in Example 1.

According to Table 2, reagents except for DMF were mixed and dried thoroughly. DMF was added and heated to 90° C. for an hour. Then, reaction was terminated when the spot which corresponds to CNCA was disappeared on TLC developed by a mix solvent (ethyl acetate and hexane (2:1)). After Cu was removed by filtration, the filtrate was dropped into a centrifuge tube containing 15 ml of distilled water. On dropping the filtrate into distilled water, grayish suspended substance was produced. After extracting with ethyl acetate, the extract was washed two times with respectively 5% $KHSO_4$, 4% $NaHCO_3$ and saturated NaCl. Then, $MgSO_4$ was added for dehydration and filtered. The filtrate was subjected to analysis with developing solvent (ethyl acetate and hexane (5:2)), showing three different spots. Next, column purification was performed on the filtrate with a developing solvent (ethyl acetate and hexane (5:2), Rf=0.7). As some substances had a tendency to adsorb on the column, a fraction with the lowest Rf value could not be completely purified, thus the second column purification was performed changing a developing solvent for ethyl acetate and methanol. The ratio of methanol was gradually increased and the obtained purified product was identified by $^1$H-NMR and MALDI-TOF-Mass.

The results of analysis by $^1$H-NMR showed that the target product was obtained but in low yield.

TABLE 2

|  | M. W | mg | mmol | mL | mol. ratio |
|---|---|---|---|---|---|
| CNCA | 206.6 | 160 | 291 |  | 2 |
| Boc-aminoPHe-OEt | 308.3 | 480 | 593 |  | 4 |
| $K_2CO_3$ | 138.2 | 56 | 152 |  | 1 |
| act.Cu |  | 28 |  |  |  |
| DMF |  |  |  | 1.5 |  |

Example 2

Synthesis of Boc-alanine-substituted Benzoacridone Derivative

[Chem. 13]

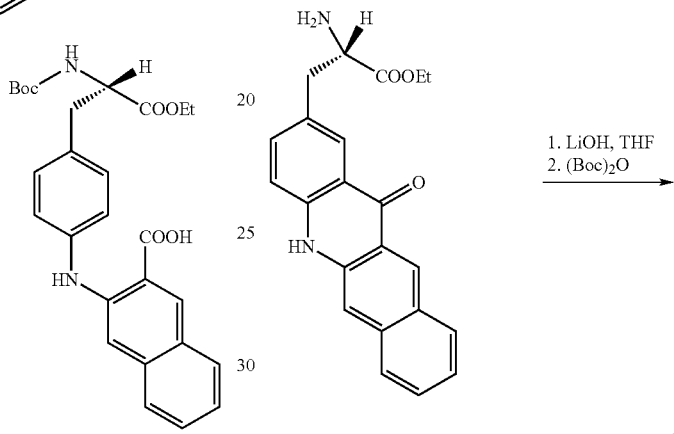

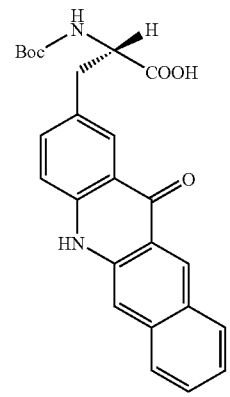

100 mg of badAla-OEt (0.28 mmol) was dissolved in tetrahydrofuran (THF) on ice, and after dropping LiOH (1 M) with stirring, the solution was stirred on ice for 2 hours. Only one spot was observed to be adsorbed on almost zero point by a developing solvent (dichloromethane and methanol (8:2)), thereby the separation of ethanol group was regarded as completed. 90 mg of $(Boc)_2O$ (0.41 mmol) was dissolved in THF, and the solution was dropped into a flask on ice with stirring. Then, LiOH was added until pH was indicated 9. After stirring for an hour on ice, it was stirred overnight at room temperature.

Figure 3:
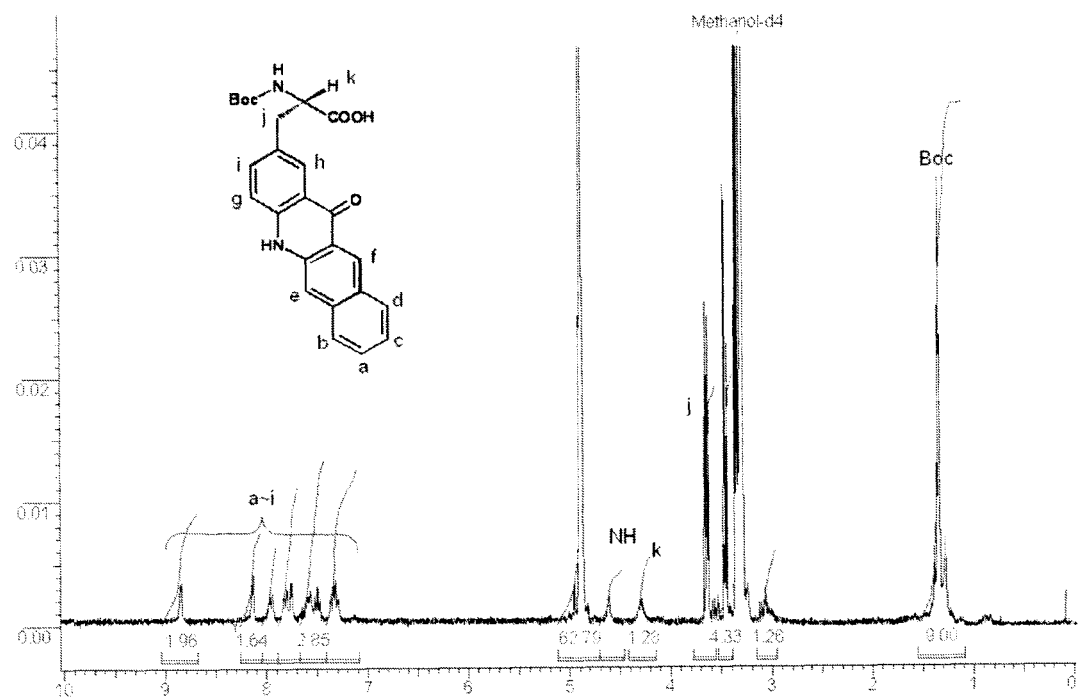
FIG. 3 shows the analytical result of $^1$H-NMR of a Boc-alanine-substituted benzoacridone derivative. (Example 2)

After the reaction terminated, THF was removed on an evaporator, and the residue was dissolved in ethyl acetate and washed two times with respectively 5% $KHSO_4$, 4% $NaHCO_3$ and saturated saline. About four spots were observed with a developing solvent (dichloromethane and methanol (8:2)). The product was analyzed by $^1$H-NMR and identified to be Boc-alanine-substituted benzoacridone derivative (Boc-badAla-OH) (FIG. 3).

Experimental Example 1

Absorption Spectrum

Figure 4:
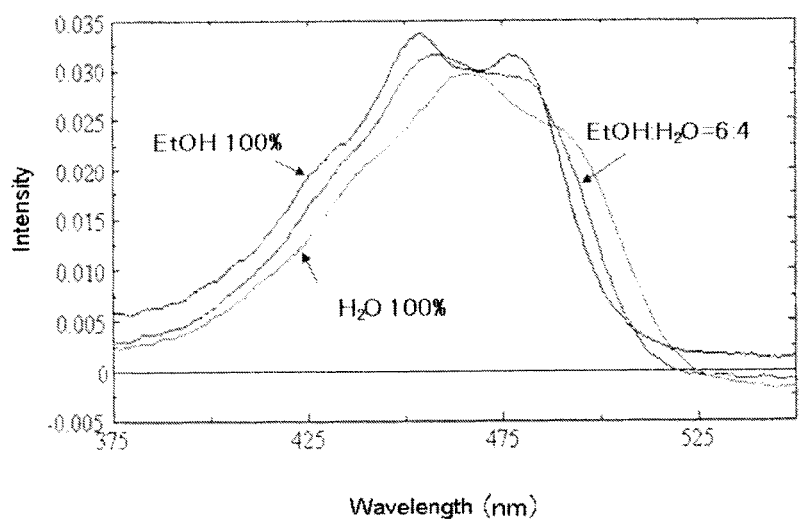
FIG. 4 shows absorption spectra of the fluorescent substance of the invention. (Experimental Example 1)

Boc-badAla-OH prepared in Example 2 was dissolved respectively in ethanol, water and a mixture of ethanol and water (6:4) in a concentration of $2.3 \times 10^{-5}$M, and their absorption spectra were measured at room temperature using JASCO "V560" supplied by JASCO Corporation. As a result, the maximum absorption wavelength of Boc-badAla-OH was around 460 nm (FIG. 4), suggesting that it was excited by wavelengths of 455, 468 and 488 nm.

Experimental Example 2

Fluorescence Spectrum

Figure 5:
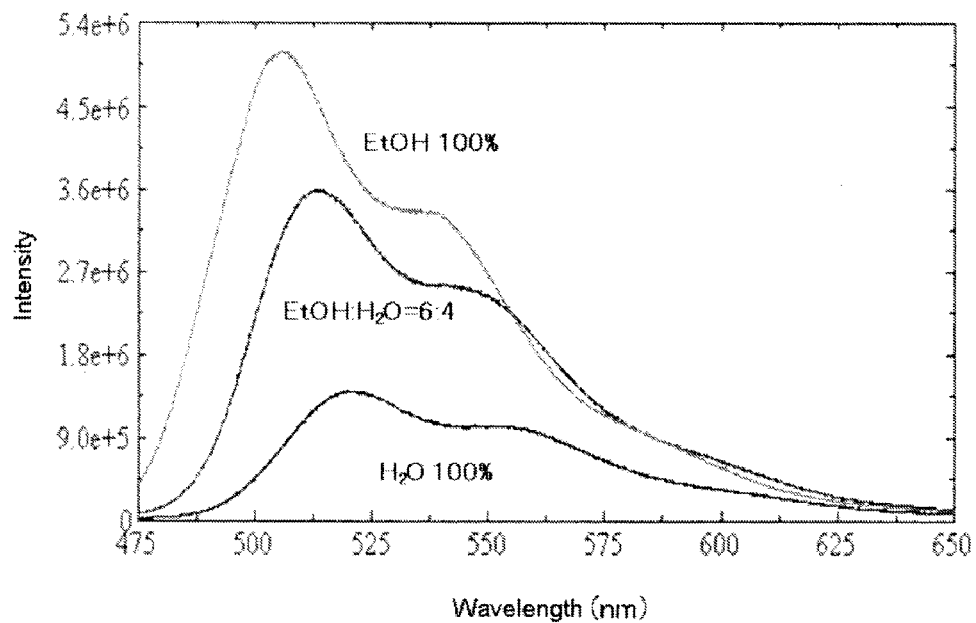
FIG. 5 shows fluorescence spectra of the fluorescent substance of the invention. (Experimental Example 2)

Boc-badAla-OH prepared in Example 2 was dissolved respectively in ethanol, water and a mixture of ethanol and water (6:4) in a concentration of $2.3 \times 10^{-6}$M, and fluorescence spectra were measured at room temperature, setting the excitation wavelength of 468 nm, using ISA "FluoroMax-2" supplied by Jobin-Yvon/HORIBA, Ltd. As a result, it was observed that Boc-badAla-OH emitted fluorescence at wavelengths of 500 to 525 nm (FIG. 5).

Experimental Example 3

Concerning Fluorescence Lifetime

Boc-badAla-OH prepared in Example 2 was dissolved in 50 mM PBS (pH7.0) in a concentration of $3 \times 10^{-4}$M, and fluorescence intensity was measured at room temperature at 500 nm, setting the excitation wavelength at 415 nm of blue laser from a simple-type beam system, using Hamamatsu "microchannel photomultiplier tube" supplied by Hamamatsu Photonics K.K. which was cooled to $-30°$ C., and then fluorescence lifetime was measured.

As a result, the obtained fluorescence lifetime was $\tau = 16.6$ nanoseconds.

While the lifetime of BODIPY, a commercial product, was 5.7 nanoseconds (MeOH) on the literature, and that of FITC was 4.1 nanoseconds (0.01M NaOH) on the literature. The other primary spectroscopic properties of fluorescent probes were listed on the homepage of IOM GmbH (see, www.iom-berlin.de).

Experimental Example 4

Photostability

Figure 6:
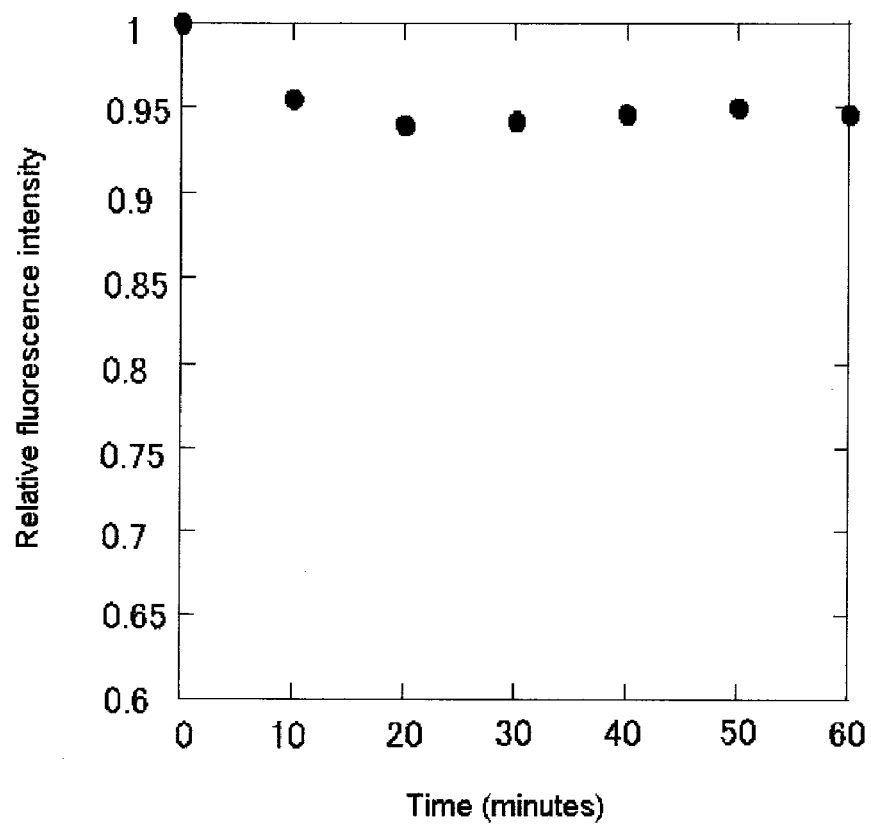
FIG. 6 shows the photostability of the fluorescent substance of the invention. (Experimental Example 4)

Boc-badAla-OH prepared in Example 2 was dissolved in water in a concentration of $1.2 \times 10^{-6}$M, and photostability was examined at room temperature using ISA "FluoroMax-2" analyzer, irradiating a beam of 468 nm excitation wavelength continuously for an hour. As a result, otherwise an hour after the irradiation, it held 95% fluorescence intensity of that at the start of the experiment (FIG. 6). Thus, it was demonstrated that badAla had excellent photostability. On the other hand, values of commercial products BODIPY and FITC shown on the literature, obtained by dissolving them respectively in TBS buffer for measurement on FluoroMax, were respectively 88% and 85%.

Experimental Example 5

Solid-Phase Synthesis of Artificial Peptide

Boc-badAla-OH prepared in the same manner as in Example 2 was linked to the N-terminal of Tat (47-57), which was a transmembrane peptide, by Fmoc solid-phase peptide synthesis method to synthesize an artificial peptide having a fluorescent amino acid.

Solid-phase synthesis was carried out according to Table 3.

1) Swelling of Resin (Ufmoc-NH-SAL-PEG Resin)

The resin was metered into a reactor, and then a mixture of dimethylformamide (DMF) and dichloromethane (DCM) (1:1) was added and stirred approximately for an hour.

2) Deprotection

After DMF containing 20% piperidine was added there and stirring for 7 minutes, solid-liquid separation was conducted. This waste solution was diluted to an appropriate concentration for UV measurement.

3) Coupling

N-methylmorpholine (NMP) was added to Fmoc-aa-OH (aa indicating amino acids) and dissolved completely. Into the same microtube, condensing agents O-(benzotriazole-1-yl)-N,N,N',N'-tetramethyluroniumhexa fluorophosphate (HATU) and HOAt were added, and then DMF was also added and dissolved completely, and diisopropylethylamine (DIPEA) was added. Those two solutions above were placed in the reactor and stirred for 45 minutes.

4) Capping

800 μl of a mixture of 5% acetic anhydride ($AC_2O$) and 6% lutidine in DMF was placed in the reactor and stirred for three minutes.

The steps from 2) to 4) were repeated to condense all amino acids respectively. Then, the target peptides were separated from the resin. The separation was conducted by adding the resin in a solution consisting of 95% trifluoroacetic acid (TFA), 2.5% $H_2O$ and 2.5% triisopropylsilane (TIS) and stirring for 2.5 hours. A solution containing the target peptide was subjected to reprecipitation with ether and centrifuged to collect the precipitate, and then the product was identified by MALDI-TOF-mass.

As a result, the actual value obtained by Exact Mass $(M+H)^+$ was 1709.19 (calculated value=1710). The sequence of the obtained peptide was the sequence represented by SEQ. ID. NO: 1 given in the sequence listing.

(SEQ. ID. NO: 1)    badAla G RKK RRQ RRR-NH$_2$ wherein, the C-terminal of the peptide sequence represented by SEQ. ID. NO: 1 was amidated.

As described above, Boc-badAla-OH, which was one of the fluorescent substances of the present invention, was confirmed to be useful in peptide synthesis. Usefulness of the intracellular utility of badAla is expected by introducing a cell-introduction-peptide (TAT) containing badAla into a cell and confirming the presence of badAla in the cell using a confocal microscope.

TABLE 3

|  | w.M. | mg (uL) | umol | mol ratio |
| --- | --- | --- | --- | --- |
| Ufmoc-NH-SAL-PEG Resin | 0.26 mmol/g | 35 | 9.1 | 1 |
| Fmoc-Gly-OH | 297 | 11 | 37.0 | 4 |
| Fmoc-Arg(pbf)-OH | 649 | 23.5 | 36.4 | 4 |
| Fmoc-Lys(Boc)-OH | 469 | 17 | 36.2 | 4 |
| Fmoc-Gln(trt)-OH | 611 | 22 | 36.0 | 4 |
| Boc-badAla-OH | 432 | 12 | 27.8 | 3 |

TABLE 3-continued

|  | w.M. | mg (uL) | umol | mol ratio |
|---|---|---|---|---|
| HATU | 380 | 12.5 | 32.9 | 3.6 |
| HOAt | 136 | 5 | 36.8 | 4 |
| DIPEA | 129(0.742 g/mL) | 8.5(11.5 uL) | 65.9 | 7.2 |
| DMF | for HATU, HOAt | (72.5 uL) | 0.5M for aa | |
| NMP | for aa | (72.5 uL) | 0.5M for aa | |

INDUSTRIAL APPLICABILITY

As described above in detail, the fluorescent substances of the present invention can be used as, for example, a Boc- or Fmoc-protected fluorescent amino acid and are useful in the synthesis of fluorescent peptides in large amounts through an automatic peptide synthesizer. Fluorescent peptides are broadly used in various analyses, examinations and the like. For example, existing fluorescent substances having absorption and emission wavelengths in the different wavelength range and the fluorescent substances of the present invention can be incorporated into one molecule of peptide or protein for inducing fluorescence resonance energy transfer (FRET). Further, an existing electron acceptor and the fluorescent substance of the present invention can be incorporated into one molecule of peptide or protein for inducing intramolecular electron transfer quenching. Such electron transfer quenching is useful in sensing, analyses of protease actions and the like. In that case, the emission of fluorescence is restored by the cleavage of the peptide or protein. Further, as the fluorescent substance of the present invention has a long fluorescence lifetime, the fluorescence emission of the fluorescent substance of the present invention would be maintained for a long time, even after the background fluorescent noise of the biological sample is decreased when a target substance is detected in a partial purified biological sample. Therefore, detection with high sensitivity can be performed by time-resolved measurement.

The invention claimed is:
1. A fluorescent substance consists of amino acid-substituted benzoacridone derivative excitable under visible light, wherein the amino acid-substituted benzoacridone derivative is represented by one of the following formulae from (I) to (III):

[Chem. 1]

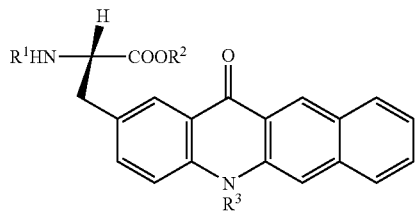

Formula I

[Chem. 2]

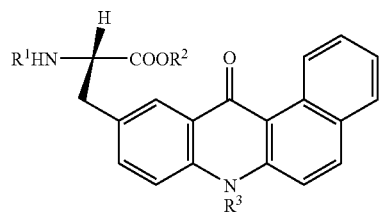

Formula II

[Chem. 3]

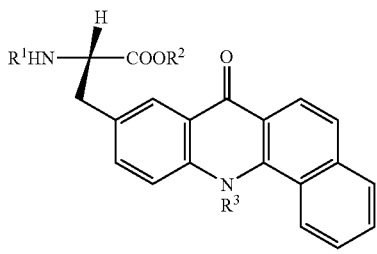

Formula III wherein in the formulae from (I) to (III):
R$^1$ represents a hydrogen atom or an amino protecting group, R$^2$ represents a hydrogen atom or carboxylate

SEQUENCE LISTING

<160> NUMBER OF SEQ ID NOS: 1

<210> SEQ ID NO 1
<211> LENGTH: 11
<212> TYPE: PRT
<213> ORGANISM: Artificial
<220> FEATURE:
<223> OTHER INFORMATION: Synthesized peptide derived from TAT region
      (47-57) of human immunodeficiency virus
<220> FEATURE:
<221> NAME/KEY: MISC_FEATURE
<222> LOCATION: (1)..(1)
<223> OTHER INFORMATION: badAla

<400> SEQUENCE: 1

Xaa Gly Arg Lys Lys Arg Arg Gln Arg Arg Arg
1               5                   10 ester structure, and $R^3$ represents a hydrogen atom, or a straight or branched, saturated or unsaturated aliphatic hydrocarbon group;

cycloalkyl, aryl, aralkyl, alkyloxy, alkenyloxy, alkynyloxy, aryloxy or aralkyloxy group which may have substituent(s); or sugar residue.

2. The fluorescent substance according to claim 1, wherein the maximum absorption wavelength of a mixture of water and ethanol (at a volume ratio of 1:1) is in the range from 420 to 520 nm.

3. A reagent comprising the fluorescent substance according to claim 1.

4. A fluorescent peptide chain or protein, wherein the fluorescent substance according to claim 1 is incorporated at either its C- or N-terminal or in its interior.

5. The peptide chain or protein according to claim 4 further comprising other fluorescent substance or quenching agent capable of interfering with the fluorescent substance consisting of amino acid-substituted benzoacridone derivative excitable under visible light.

6. A production method of the fluorescent substance according to claim 1, comprising a step using $Cu_2O$ and ethyleneglycol monoalkyl ether in coupling of a halonaphthalene derivative and 3-(4-amino-phenyl)-2-tert-butoxycarbonylamino-propionate ester.

7. The production method according to claim 6, wherein the halonaphthalene derivative is 3-chloro-naphthalene-2-carboxylic acid, the 3-(4-amino-phenyl)-2-tert-butoxycarbonylamino-propionate ester is 3-(4-amino-phenyl)-2-tert-butoxycarbonylamino-propionic acid ethyl ester, and the ethylene glycol monoalkyl ether is methoxyethanol.

8. A reagent comprising the fluorescent substance according to claim 2.

9. A fluorescent peptide chain or protein, wherein the fluorescent substance according to claim 2 is incorporated at either its C- or N-terminal or in its interior.

10. The peptide chain or protein according to claim 4 further comprising other fluorescent substance or quenching agent capable of interfering with the fluorescent substance, wherein the maximum absorption wavelength of a mixture of water and ethanol (at a volume ratio of 1:1) is in the range from 420 to 520 nm.

11. The peptide chain or protein according to claim 4 further comprising other fluorescent substance or quenching agent capable of interfering with the fluorescent substance, wherein the amino acid-substituted benzoacridone derivative is alanine-substituted benzoacridone derivative.

* * * * *